(12) United States Patent
Osman et al.

(10) Patent No.: US 6,740,213 B2
(45) Date of Patent: *May 25, 2004

(54) COMPOSITE MEMBRANE SENSOR

(75) Inventors: Peter Damien John Osman, West Lindfield (AU); Maxwell John Crossley, Beecroft (AU); Alastair Scott Martin, Queenscliff (AU); Ronald John Pace, Farrer (AU)

(73) Assignees: Australian Membrane and Biotechnology Research Institute, New South Wales (AU); The University of Sydney, New South Wales (AU)

( * ) Notice: Subject to any disclaimer, the term of this patent is extended or adjusted under 35 U.S.C. 154(b) by 0 days.

This patent is subject to a terminal disclaimer.

(21) Appl. No.: 09/761,496

(22) Filed: Jan. 16, 2001

(65) Prior Publication Data

US 2001/0030132 A1 Oct. 18, 2001

Related U.S. Application Data

(63) Continuation of application No. 09/011,005, filed on Jul. 23, 1998, now Pat. No. 6,210,551.

(30) Foreign Application Priority Data

Aug. 1, 1995 (AU) ............................................... PN4534
Apr. 11, 1996 (AU) ............................................... PN9206

(51) Int. Cl.[7] ............................................. G01N 27/327
(52) U.S. Cl. .............................. 204/403.08; 204/403.05
(58) Field of Search ....................... 204/403.01, 403.06, 204/403.07, 403.08; 205/777.5, 778

(56) References Cited

U.S. PATENT DOCUMENTS

| | | | | |
|---|---|---|---|---|
| 5,756,355 A | * | 5/1998 | Lang et al. | 435/7.21 |
| 5,874,316 A | * | 2/1999 | Cornell et al. | 435/317.1 |
| 6,210,551 B1 | * | 4/2001 | Osman et al. | 204/403.06 |

* cited by examiner

Primary Examiner—Alex Noguerda
(74) Attorney, Agent, or Firm—Gottlieb, Rackman & Reisman, P.C.

(57) ABSTRACT

The present invention provides a biosensor comprising an electrode and a membrane in which the biosensor includes at least two zones each zone differing from each other zone in a property. The membrane includes a plurality of ionophores, at least a proportion of which are capable of lateral diffusion within the membrane. A plurality of first binding partner molecules are attached to membrane elements positioned within a first zone such that the first binding partner molecules are prevented from diffusing laterally into a second zone. Second binding partner molecules are attached to the ionophores and the rate of lateral diffusion within the membrane of the first binding partner molecules and second binding partner molecules is different.

20 Claims, 10 Drawing Sheets

COMPOSITE MEMBRANE SENSOR

RELATED APPLICATIONS

This application is a continuation of application Ser. No. 09/011,005, filed Jul. 23, 1998, now U.S. Pat. No. 6,210,551 incorporated herein by reference.

BACKGROUND OF THE INVENTION

The present invention relates to a biosensor comprising an electrode and membrane in which the conductance of the membrane changes in response to the presence of an analyte. In particular, the invention relates to the use of composite layer membranes incorporating a supporting layer comprising regions of low ionic or electronic mobility with regions of high ionic or electronic mobility.

International patent application WO 90/08783, the disclosure of which is incorporated herein by reference, discloses a membrane in which the conductance of the membrane is dependent on the presence or absence of an analyte. The membrane comprises a closely packed array of amphiphilic molecules and a plurality of ionophores comprising first and second half membrane spanning monomers. Ionophores within the top layer monomer are capable of lateral diffusion within the membrane. The membrane also includes receptor molecules and the binding of the analyte to the receptor molecules causes a change in the relationship between the first and second half membrane spanning monomers thereby altering the conductivity of the membrane. This type of gating mechanism is referred to as "lateral segregation".

In the lateral segregation gating mechanism described in WO 90/08783 it is essential that the membrane include dimeric ion channels with at least one of the monomers being capable of diffusion within the membrane so that the relationship between the two monomers may be altered. The present inventors have developed a biosensor in which gating is achieved by allowing ion channels to diffuse in a lipid membrane between zones of the electrode with differing states of polarisation, conductivity, ion reservoir capacity, or redox potential. On binding of an analyte, the ion channels are locked into one of these regions. With this arrangement any ion channel, membrane spanning or otherwise, can be used.

The provision of the hydrophilic tethers has permitted the construction of a robust membrane but the elimination of that element would further increase the stability of the membrane. This is significant because the membranes themselves are only one or two molecules in thickness. Further, the membranes in use should be able to contact blood and other biological materials that have interfering substances which tend to disturb the integrity of the membrane and its ionic reservoir.

The use of molecular wires in connection with macromolecular devices has been reviewed in J. -M. Lehn, Perspectives in Supramolecular Chemistry—From Molecular Recognition towards Molecular Information Processing and Self-Organisation, (Agnew, Chem. Int. Ed. Engl. 29, 1990, 1304–1319). The molecular wire is a connector permitting electron flow between the different elements of a molecular electronic system. An example is based on caroviologens, long, conjugated, polyolefinic chains bearing pyridinium groups at each end. These have been incorporated into dihexadecyl phosphate vesicles but were not successful as conductors in that environment. Small quantities of zwitterionic caroviologens have been incorporated into phospholipid vesicles and accelerated the rate of reduction of an internal oxidant making it probable that electron conduction occurred. It has also been suggested that one could make polarised molecular wires which would have rectifying properties from conjugated polyolefinic chains, bearing an electron-acceptor group at one end and a donor on the other end.

Highly conducting molecular crystals prepared from porphyrin and phthalocyanine complexes have been prepared as derivatives of the metalloporphyrine skeleton (Hoffman B A and Ibers J A. Porphyrinic Molecular Metals, Acc. Chem. Res. 16, 1983, 15–21).

Molecular wires formed of bispyridium polyenes have been synthesised and incorporated into the bilayer membrane of sodium dihexadecyl phosphate vesicles so that they have formed membrane-spanning electron channels. These molecular wires were not adapted to provide conduction between a membrane and its supporting electrode but had the pyridinium sites close to the negatively charged outer and inner surfaces of the vesicles and the polyene chain crossed the lipidic interior of the membrane. (Arrhenius T S, Blanchard-Desce, M, Dvolaitzky, M, Lehn J-M and Maithete, J. Molecular devices: Caroviologens as an approach to molecular wires—synthesis and incorporation into vesicle membranes, Proc. Natl Acad. Sci. USA 83, 1986, 5355–5359).

Conducting organic materials similar to and including tetrabenzoporphyrine has been reported in the literature and its electrical properties noted. (Hanack M and Zipplies T. Synthesis and Properties of Doped $\mu$ Oxo (tetrabenzoporphyrinato) germanium(IV). J. Am. Chem. Soc. 107, 1985, 6127–6129).

SUMMARY OF THE INVENTION

In a first aspect the present invention consists in a biosensor comprising an electrode and a membrane, the biosensor including at least two zones each zone differing from each other zone in a property; the membrane including a plurality of ionophores, at least a proportion of the ionophores being capable of lateral diffusion within the membrane, a plurality of first binding partner molecules attached to membrane elements positioned within a first zone such that the first binding partner molecules are prevented from diffusing laterally into a second zone, second binding partner molecules attached to the ionophores, the rate of lateral diffusion within the membrane of the first binding partner molecules and second binding partner molecules being different.

In a preferred embodiment of the invention there is provided an intermediate region between at least portions of the membrane and the electrode, the intermediate region functioning as a reservoir or as a source or sink for ions.

In a further preferred embodiment of the invention the at least two zones of the biosensor are due to differing zones in the electrode, the membrane, the intermediate region or combinations thereof.

In yet another preferred embodiment the property is selected from the group consisting of chemical, polarisation, admittance, ionic reservoir capacity or redox potential.

In a preferred forms of the invention, the electrode comprises a silicon silver composite or a silicon gold composite. Similarly, the electrode may comprise a pattern of silver or gold islands deposited onto silicon oxide or a pattern of silicon oxide islands deposited onto gold or silver. Indeed, a number of possible arrangements will readily occur to those skilled in this area. These include gold/aluminium, silver/gold, silicon rubber/gold, rubber/silver, titanium/gold and niobium/gold, or patterned lipid monolayers attached to the gold so that the lipid regions provide electronic/ionic insulation and the lipid free regions provide an ion reservoir. The essential. criterion is that the electrode comprises zones of differing states of polarisation, conductivity, ionic reservoir capacity or redox potential.

In the situation where the at least two zones of the biosensor comprise a pattern of islands, the islands are preferably arranged to be insulated from each other so that they may be measured independently, or electrically interconnected for simultaneous measurement of all gating sites. In International patent application No PCT/AU89/00352 arrangements for independent measurements are disclosed. This disclosure of PCT/AU89/00352 is hereby incorporated by reference.

In yet a further preferred embodiment of the present invention, the first and second zones comprise two interleaved but separated comb electrodes at different potentials. Preferably, the separation between adjacent teeth of the respective combs and the width of each tooth is less than one micron. The total number of teeth on each electrode is preferably approximately 500.

The first and second binding partner molecules may be attached to the membrane elements and ionophores by any of the techniques disclosed in Australian patent No 617687 or PCT/AU93/00509, the disclosures of which are incorporated by reference. The first binding molecules are attached to membrane elements which span the membrane. Preferred membrane elements are bolar lipids or membrane spanning proteins.

The first binding molecule is prevented from diffusing laterally within the membrane by attachment of the membrane element which is attached to the electrode. For example, in the preferred forms of the invention, the membrane element is an bolar lipid or membrane spanning protein which is attached to the electrode.

The membrane elements to which the first binding partner moieties are attached may be differentially attached to preselected zones of the electrode by selection of the attachment group. For example where the electrode is a gold/silicon and it is desired to position the first binding moieties over the gold zones of the electrode, the membrane element is provided with a thiol or disulphide group such that membrane element is attached to gold zones of the electrode by chemisorption.

Alternatively, the attachment group may be selected such that the membrane element is attached to the silicon zones.

The differing zones may also be created by taking advantage of the self-assembly properties of the molecules themselves. The adsorption of molecules onto substrates is dictated by the type of functional group involved in the substrate-molecule bond, the overall structure of the molecule, the size of the molecule, and the ratio of molecules when mixtures are used, all of which affect the kinetics of adsorption for each type of molecule and can influence the formation of phase-separated molecular domains or zones. PCT/AU93/00509 "Improved Sensor Membranes" and PCT/AU96/00369 "Self-assembly of sensor membranes" (the disclosures of which are incorporated herein by reference) show that the function of the biosensor membrane can be dependent on the ratio of tethered lipid to small spacer molecule which adsorbs to the gold substrate. For example, the optimum ratio for DLP (Linker Lipid A) and MAAD (mercaptoacetic acid) in the biosensor membrane is 2:1. If the MAAD concentration is increased by a factor of two or more, then the percentage of bilayer membrane which forms a 'floating' bilayer or non-tethered zone due to the greater amount of MAAD) molecules adsorbed onto the gold surface, increases, which in turn decreases the stability and specific response of the biosensor to analyte detection, and can affect the reservoir properties within the tethered and non-tethered regions.

Separate zones can also be formed by using mixed substrates (e.g. selectively etched metal alloys or layered metals, selective substrates prepared by conventional lithography methods, etc), and attaching substrate-specific functional groups onto molecules which are be tethered to the substrate in specific zones.

Selecting different types of molecules with chemical groups or bonds which can be selectively broken by application of energy in the form of heat, light, UV, laser, etc., after deposition onto a uniform substrate, can also result in the formation of different zones, the size of which can be controlled by the ratio of the different molecules.

It is also possible to form the differing zones using micro-patterning of self assembled monolayers (SAMs) on a solid substrate. Details regarding this procedure can be found in "Self-Organization of Organic Liquids on Patterned Self-Assembled Monolayerd" by Hans A. Biebuyck and George M. Whitesides; Langmuir 1994, 10, 2790–2793 and "Scanning Force Microscopies Can Image patterned Self-Assembled Monolayers" by James L. Wilbur, Hans A. Biebuyck, John C. MacDonald and George M. Whitesides; Langmuir 1995, 11, 825–831 (the disclosures of these articles are included herein by reference).

Briefly, the patterning is done using a silicone rubber stamp with which a SAMs can be transferred to specific areas of a substrate. The uncoated areas can then be filled in with another SAM. When the two SAMs have different endgroups one can use lateral force microscopy to distinguish the regions of each SAM. An analogous technique could be used to form the two regions (conducting and non-conducting) of the composite substrate.

In yet another preferred embodiment of the present invention there is provided an intermediate region between at least portions of the membrane and the electrode, the intermediate region functioning as a reservoir or as a source or sink for ions. As will be readily apparent to those skilled in the art the provision of such an intermediate region between selected regions of the membrane and electrode will result in regions or zones of differing reservoir capacity. Such an arrangement may be achieved by using an electrode having "peaks" and "troughs" in which the membrane extends from "peak" to "peak" with an intermediate region being provide in each of the intervening "troughs".

The intermediate region may an ionic reservoir such as are disclosed in International Patent Application Nos. PCT/AU92/00132, PCT/AU93/00509 and PCT/AU96/00304. (The disclosures of these applications are incorporated herein by reference.).

In an alternative embodiment the intermediate region comprises molecular wires.

The molecular wires preferably have a porphyrinic or octathiophene based structure. The porphyrinic structure, which is preferred, is preferably comprised of a series of fused porphyrin rings with adjacent components of the wire fused through the [b] bond of the porphyrinic ring. This type of orientation of connectivity results in the movement of the electrons through the large molecular orbitals of the molecular wire rather than via the $\pi$-$\pi$ interactions seen in other macrocyclic conductors. Each porphyrin ring in the molecular wire is preferably substituted in its four meso positions.

The substituents at the four meso positions preferably stabilise the porphyrin ring, solubilise the porphyrin and/or subsequent derivatives and provide an electrically insulating sheath around the core of the molecular wire. Preferably, the substituent at each of the four meso positions is a 3,5-di-tert-butylphenyl ring.

The molecular wire further preferably includes bridging units between two adjacent porphyrin rings and between a porphyrin ring and end functional groups. The bridging units are preferably substantially rigid such that the molecular wire cannot fold back on itself. The bridging units also preferably provide a conjugated and planar pathway for electrons between adjacent components of the molecular wire. Preferred examples of the bridging units include an anthracene unit or tetraazaanthracene unit fused at the [b] and [e] bonds of the parent tetraazaanthracene system to the other components on the wire.

The porphyrin rings in the molecular wire may exist as freebase or as the metal chelate. In any particular molecular wire, any combination of metalloporphyrinic or freebase porphyrinic rings may be used. Metal chelation of the porphyrin rings in a molecular wire allows finer modulation of the electronic properties of the wire. A preferred chelate metal is copper.

Preferably, the molecular wires are tethered to the surface of the electrode through a binding group. Where the electrode includes gold regions this may be achieved using binding groups having a nitrogen or sulphur bearing compound. Preferred examples of such compounds include a [d] fused 1,10-phenanthroline group, a benzimidazolopyridyl group, a phenyl substituted benzimidazolophenyl group, a bisethylthio phenyl group or multiples and combinations thereof.

In a preferred embodiment of this invention, the intermediate region comprising molecular wires (MW) are formed by self-assembly onto the electrode surface. This renders the surface very hydrophobic and facilitates the subsequent formation of a lipid monolayer or lipid bilayer membrane having ionophores whose conductivity to ions responds differentially to the presence of an analyte.

As with the ionic reservoir where the intermediate region comprises molecular wires it is possible to form the differing zones by manipulation of regions of the molecular wire layer. For example, one could incorporate photosensitive moieties into a molecular wire so that exposure to some wavelength of light could disrupt the conducting pathway. Molecular wires with a quinone in the molecular backbone which are expected to undergo a (reversible) isomerisation when exposed to light that should effect the electronic flow could be used. In a similar manner it could be arranged (by suitable synthesis) that the molecular changes are permanent after illumination so that one can use a "photo-lithographic" type of exposure with a mask dictating "patterning" of the molecular conductivity across the substrate surface.

The molecular wire layer functions as a reservoir or as a source or sink for ions, with the following potential advantages:

(1) A tether region comprising a hydrophilic ionic reservoir is not required between the conductive gold surface and the lipid membrane;
(2) The membrane is rendered more stable, offering storage over long periods without degradation;
(3) Greater capacity for ionic storage than is achieved by creation of aqueous compartments;
(4) Facilitates the assembly of lipid monolayer or bilayer membranes.

A conducting bilayer (molecular wire plus lipid) is produced when a combination of conducting molecular wire and ionophore is made. The molecular wire containing monolayer, therefore acts as a robust and solid ion complexing layer which can effectively replace the tethered ion reservoir. Alternatively, the molecular wire may increase the effectiveness of the conductor/ion interface by virtue or high electronic conduction along the molecular wires.

As used herein the term "binding partner molecule" is used in its widest context. The binding partner molecule may be any chemical entity capable of binding to the desired analyte. It is any compound or composition capable of recognising another molecule and represents half of a binding pair.

Binding pairs include antibodies and either an anti-antibody, the antigen recognised by that particular antibody or an analyte analogue; naturally occurring soluble or cellular receptors and the molecules recognised by them; enzymes and their substrates, inhibitors or analogues of these; lectins and carbohydrates, chelating agents and ions, for example, calcium would be the partner to the chelating agent EDTA.

In a preferred embodiment of the present invention the first and second binding pair molecules are antibodies or any active binding fragments of antibodies.

In further preferred embodiments of the present invention the ionophore is gramicidin or analogues thereof or valinomycin.

The membrane may be single or multi-layer, however, it is presently preferred that the membrane is either a monolayer or bilayer. Where the membrane is a bilayer the ionophore may be a gramicidin dimer.

In yet another preferred form of the invention the membrane elements extend through the membrane. It is also preferred that the membrane elements are attached to the electrode via attachment groups.

The diffusion of the gramicidin ion channels in the membrane can be free or forced by external influences such as magnetic or electrostatic fields. Magnetic particles bound to an antibody may be used to link an analyte to the ion channel which could then be moved between different regions of the electrode to provide electrical gating or signal modification. Electrophoretic methods may be used in a similar manner.

In a second aspect, the present invention consists in a method of assaying a sample for the presence of an analyte, the method comprising contacting the biosensor of the first aspect of the present invention in which the first and second binding partner molecules bind to the analyte with the sample and measuring the conductivity of the membrane.

In order that the nature of the present invention may be more clearly understood, preferred forms thereof will now be described with reference to the accompanying Examples and Figures.

DESCRIPTION OF THE PREFERRED EMBODIMENTS

Figure 1A:
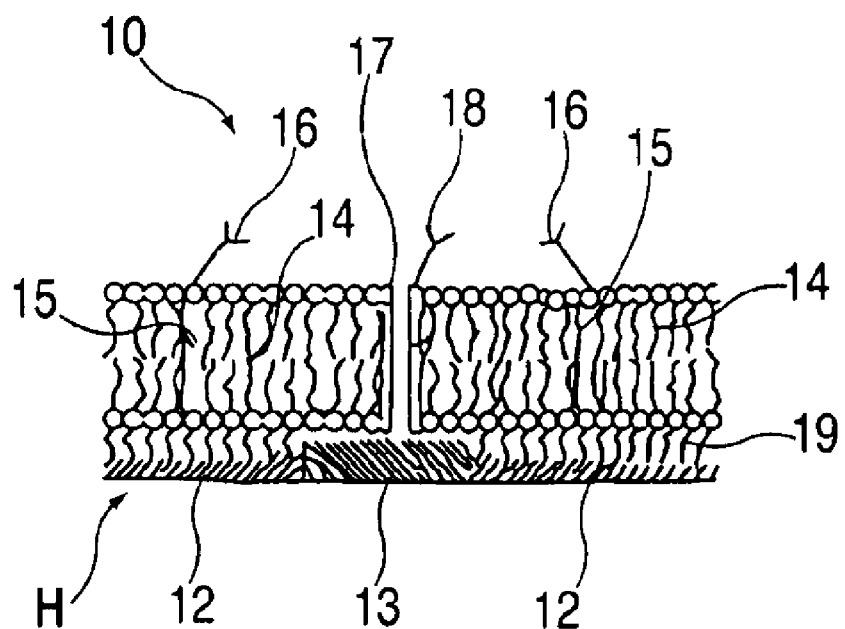
FIGS. 1 to 8 show schematic representations of various embodiments of the biosensor of the present invention.
Figure 1B:
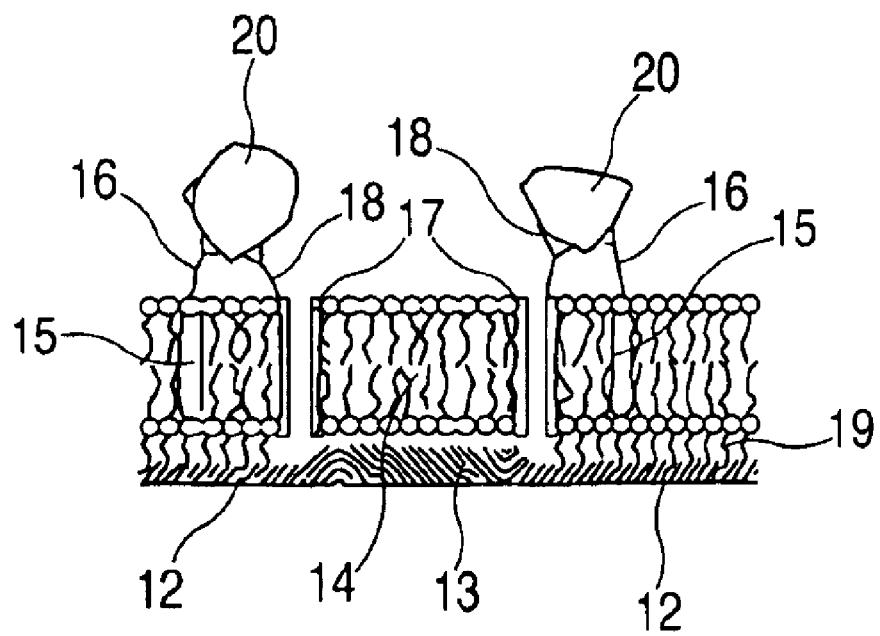

As shown in FIG. 1 the biosensor 10 comprises an electrode 11 and membrane 14. The electrode 11 comprises areas 12 and 13 which differ in polarisability, conductivity, redox potential or ionic reservoir capacity. Provided within the membrane 14 are bolar lipids 15. Attached to the bolar lipid 15 is antibody molecule 16. Also included within membrane 14 is ion channel 17 to which is attached antibody molecule 18. A. reservoir, or space, between the electrode 11 and the membrane 14 is provided and is bridged by linker molecules 19. Turning now to FIG. 1B, when analyte 20 is present it binds to antibody molecules 16 and 18 causing the ion channel 17 to be shifted in the membrane 14. As can be seen from a comparison of FIGS. 1A and 1B in the absence of the analyte the ion channel 17 lies over area 13 of the electrode 11. Upon the addition of analyte 20, the ion channel 17 now lies over region 12 of the membrane 11. This change in position is what enables the sensing of the presence of the analyte.

Figure 2A:
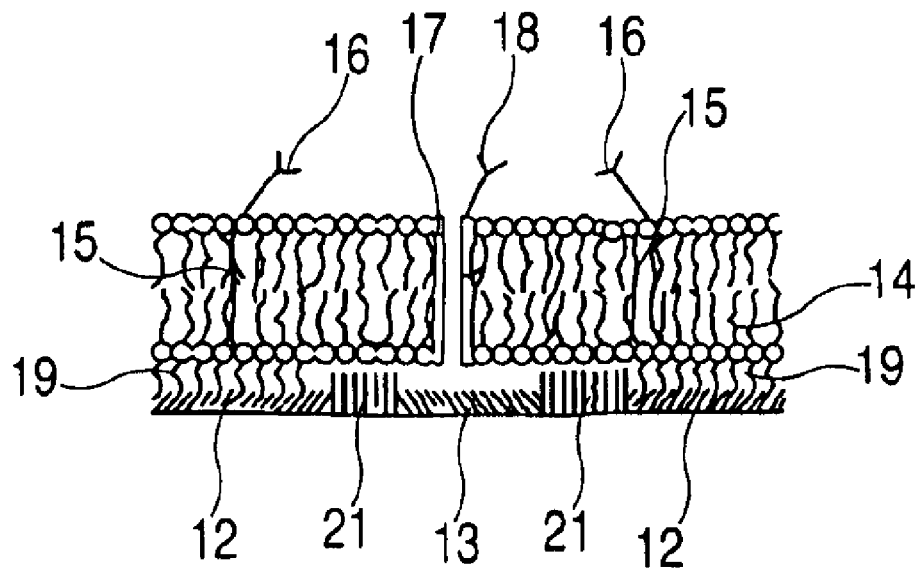
Figure 2B:
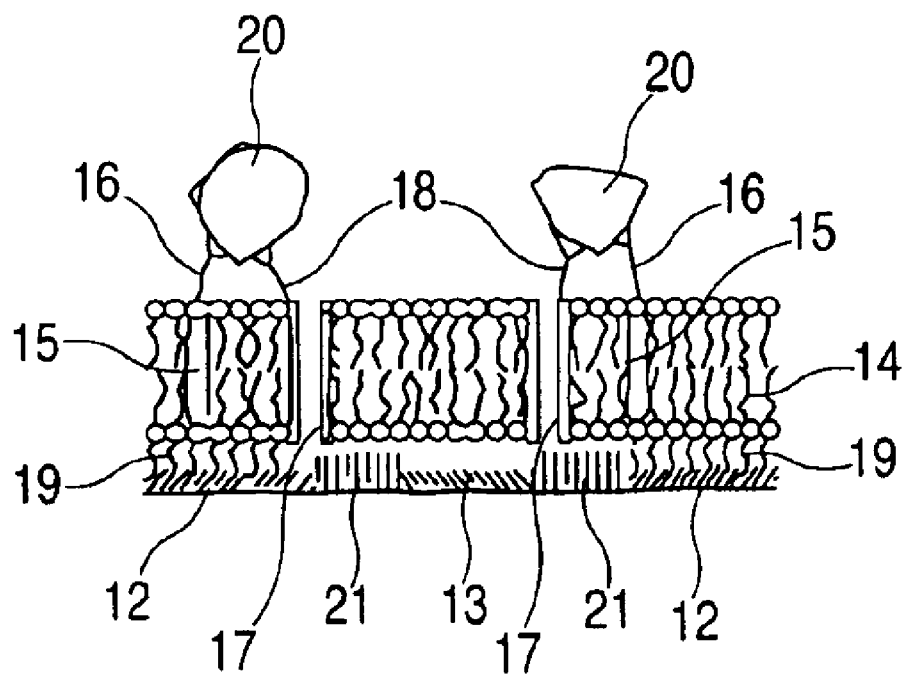
Figure 3A:
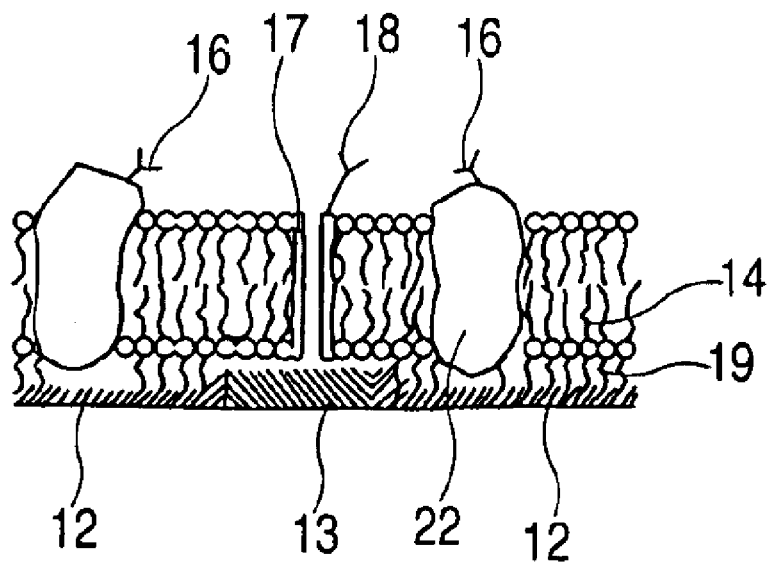
Figure 3B:
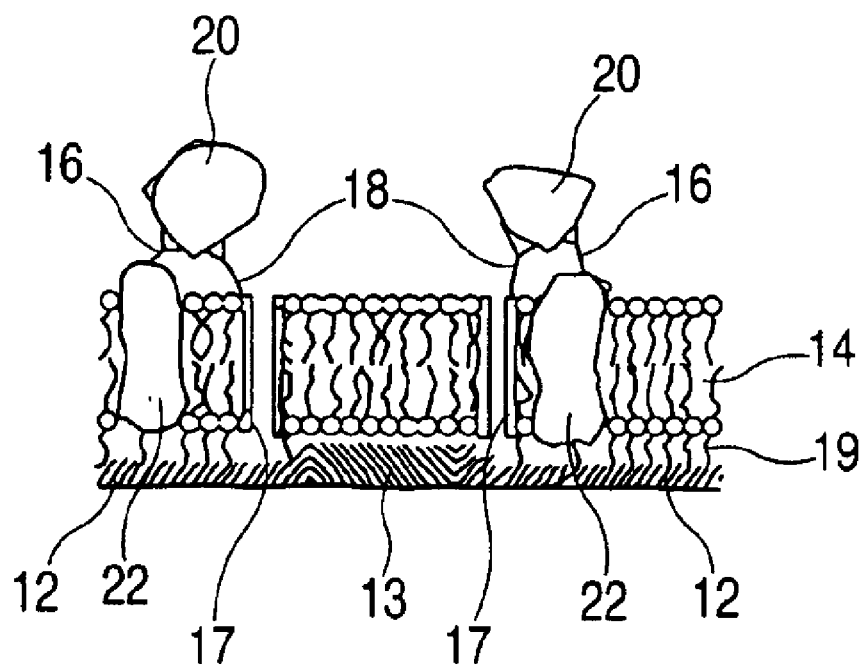

As shown in FIG. 2 the leakage current between areas 12 and 13 can be reduced and the dynamic range of the sensor increased by providing region 21 between areas 12 and 13. Once again, as shown in FIG. 2B the binding of analyte 20 to antibody molecules 16 and 18 causes a shift in the positioning of the ion channel 17. As shown in FIG. 3 the bolar lipid can be replaced by a membrane spanning protein 22. Once again the binding of analyte 20 to antibody molecules 16 and 18 causes a shift in the positioning of the ion channel 17.

Figure 4A:
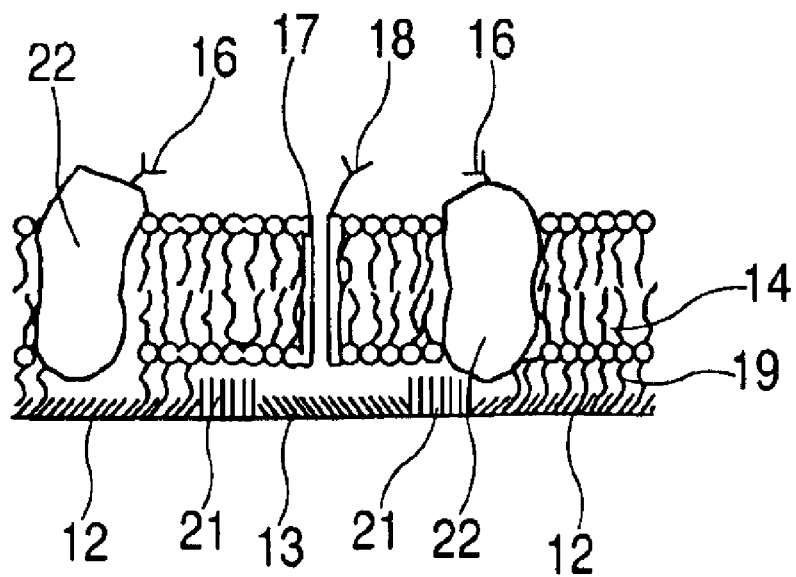
Figure 4B:
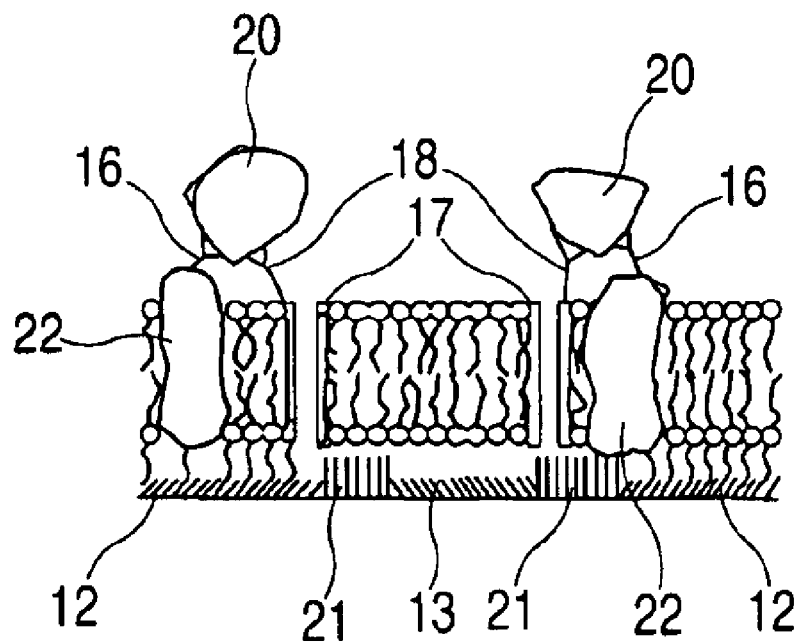

Similar gating mechanisms are shown in FIG. 4.

Figure 5A:
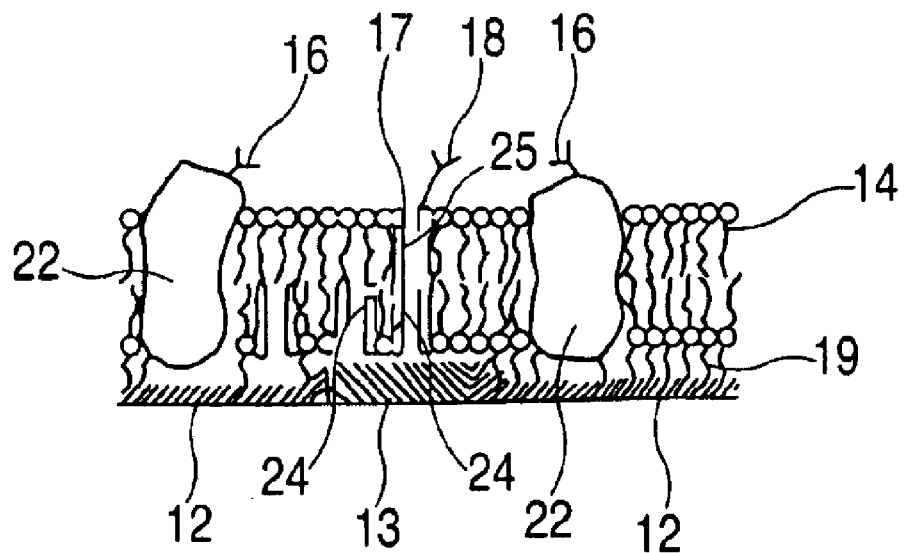
Figure 5B:
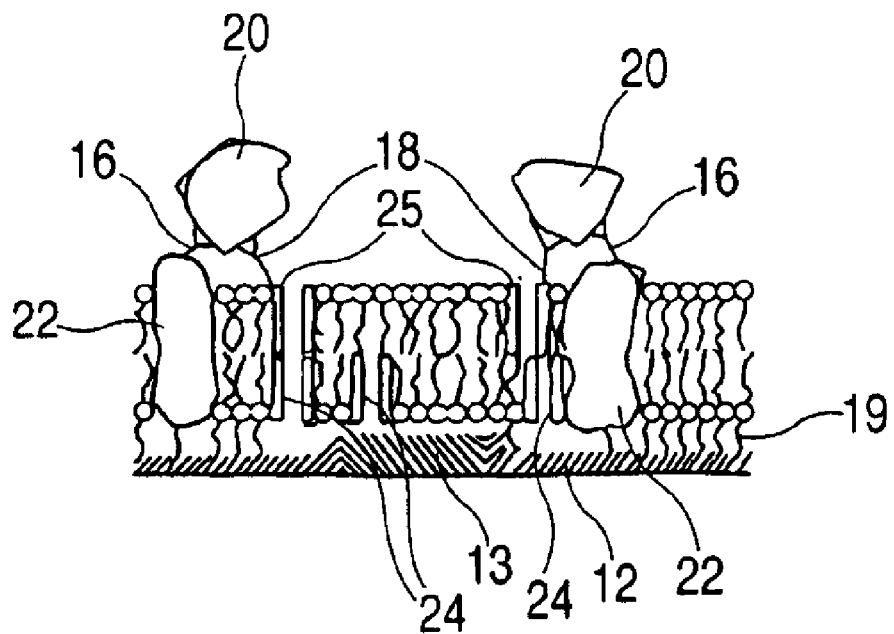

As shown in FIG. 5, the ion channel may be comprised of half membrane spanning channels 24 and 25. The half membrane spanning ion channels 24 and 25 are able to diffuse independently of each other in the membrane. Binding of analyte 20 to antibody molecules 16 and 18 causes a shift of half membrane spanning ion channel 25.

Figure 6A:
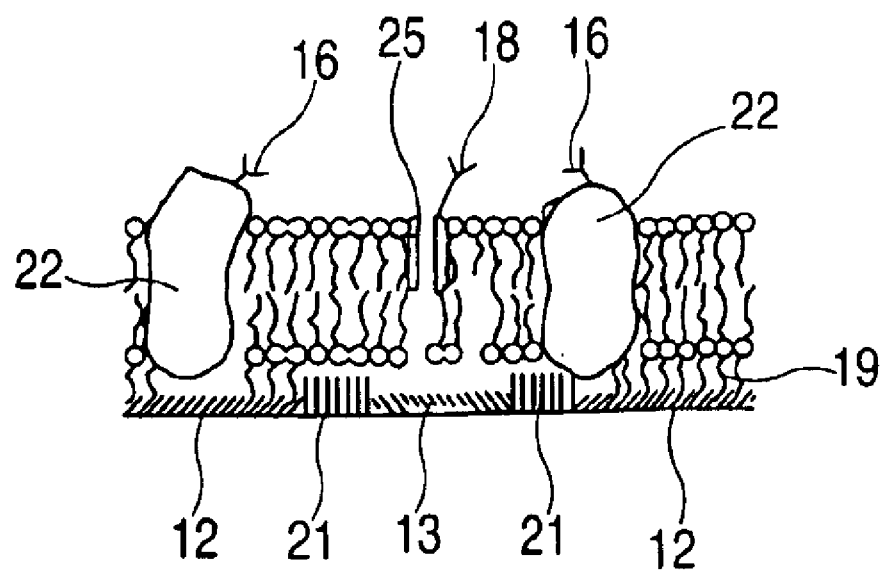
Figure 6B:
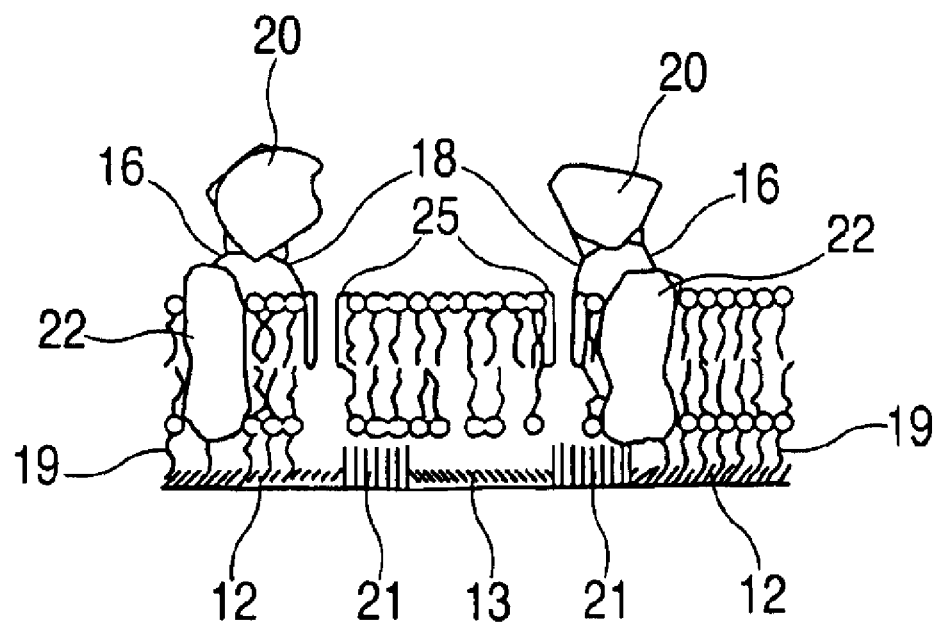

FIG. 6 shows a slightly different version of the sensor shown in FIG. 5. The half membrane spanning ion channels 24 in the lower layer can be replaced, as shown in FIG. 6, by using a leaky bottom lipid monolayer or molecular wire monolayer.

Figure 7A:
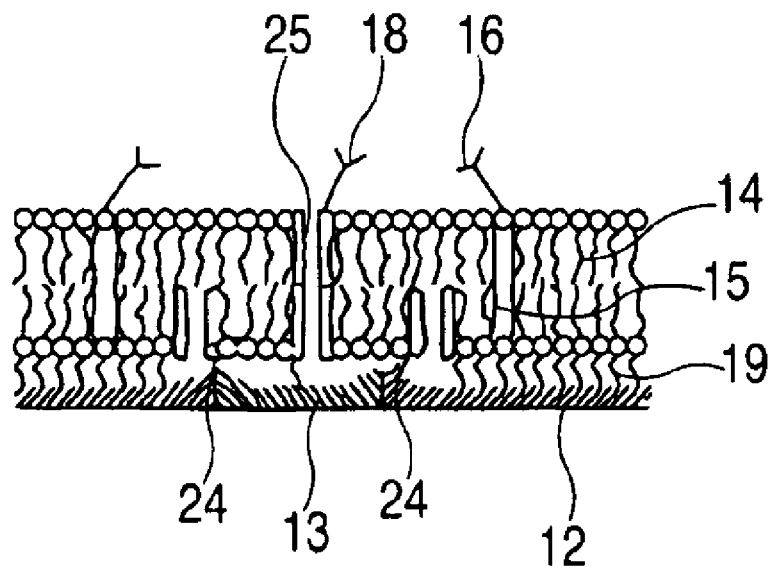
Figure 7B:
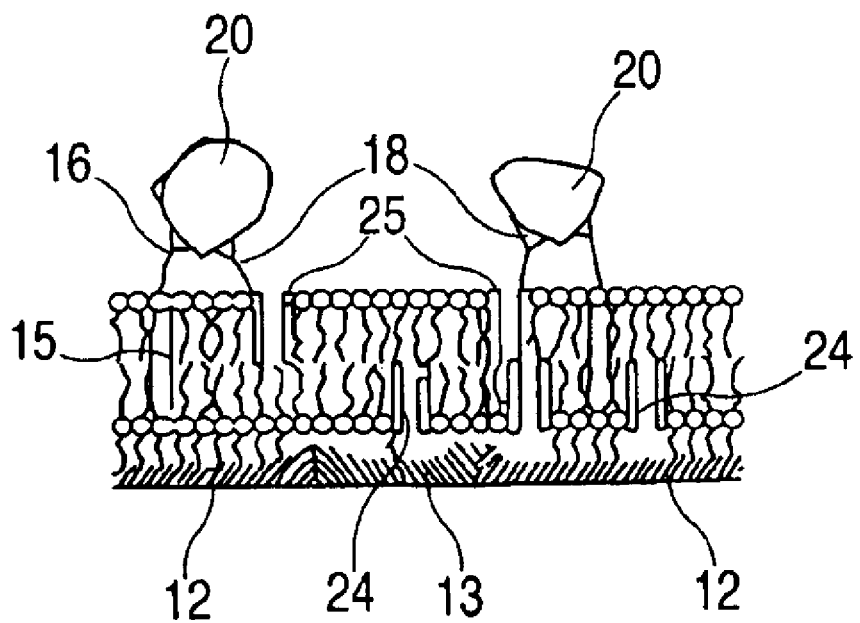
Figure 8A:
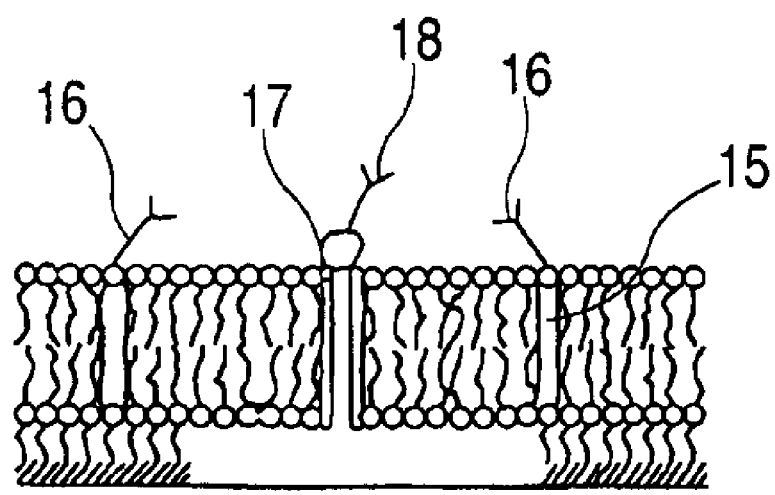
Figure 8B:
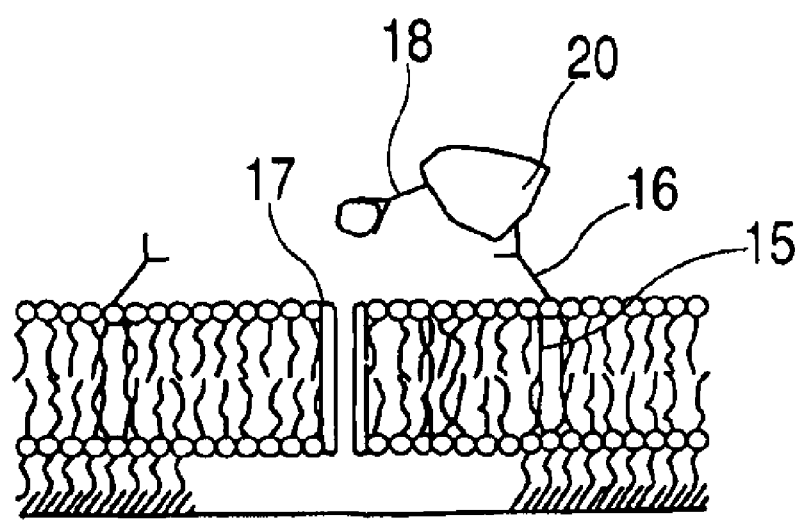

FIGS. 7 and 8 show a biosensor with a similar principle of operation as FIGS. 5 and 6, but in which the channels are switched on rather than off.

EXAMPLE 1

Preparation of Ga5XSB

To a solution of gramicidin (500 mg, 0.26 mmol), 4-(N,N-dimethylamino)pyridine (65 mg, 2 equivalents) and N-(N-BOC-6-aminocaproyl)-6-aminocaproic acid (548 mg, 6 equivalents) in DCM (80 ml) under nitrogen was added dicyclohexylcarbodiimide (220 mg, 4 equivalents) and the mixture was refluxed under nitrogen for 1 hour. The mixture was evaporated to dryness then dissolved in methanol and passed down a sephadex LH20 column. The eluate was evaporated to dryness and purified on a flash silica column eluted with DCM/methanol/water (800:60:5) to afford a major fraction of O-(N-(N-BOC-6-aminocaproyl)-6-aminocaproyl)gramicidin (420 mg, 72%).

O-(N-(N-BOC-6-aminocaproyl)-6-aminocaproyl) gramicidin (420 mg) was twice triturated with toluene and evaporated to dryness, then dried under high vacuum. Trifluoroacetic acid (3 ml) was added and the mixture was swirled for 3 min then evaporated to dryness and dried under high vacuum. The residue was triturated with toluene, evaporated to dryness and dried under high vacuum. The residue was dissolved in a minimum volume of ethanol, neutralised with triethylamine, precipitated with water and dried under high vacuum to afford O-(N-(6-aminocaproyl)-6-aminocaproyl)gramicidin (390 mg, 97%).

A mixture of O-(N-(6-aminocaproyl)-6-aminocaproyl) gramicidin (330 mg, 0.16 mmol), 4-(N,N-dimethylamino) pyridine (39 mg, 2 equivalents), and N-(N-BOC-6-aminocaproyl)-6-aminocaproic acid (330 mg, 6 equivalents) was dried under high vacuum then dissolved in dry, distilled DCM (80 ml) under nitrogen. Dicyclohexylcarbodiimide (133 mg, 4 equivalents) was added and the mixture was refluxed under nitrogen for 2 hours. The mixture was evaporated to dryness then dissolved in methanol and passed down a sephadex LH20 column. The eluate was evaporated to dryness and purified on a flash silica column eluted with DCM/methanol/water (800:60:5) to afford a major fraction of O-(N-(N-(N-(N-BOC-6-aminocaproyl)-6-aminocaproyl)-6-aminocaproyl)-6-aminocaproyl) gramicidin (290 mg).

O-(N-(N-(N-(N-BOC-6-aminocaproyl)-6-aminocaproyl)-6-aminocaproyl)-6-aminocaproyl)gramicidin (200 mg) was twice triturated with toluene and evaporated to dryness, then dried under high vacuum. Trifluoroacetic acid (3 ml) was added and the mixture was swirled for 3 min then evaporated to dryness and dried under high vacuum. The residue was triturated with toluene, evaporated to dryness and dried under high vacuum. The residue was dissolved in a minimum volume of ethanol, neutralised with triethylamine, precipitated with water and dried under high vacuum to afford O-(N-(N-(N-(6-aminocaproyl)-6-aminocaproyl)-6-aminocaproyl)-6-aminocaproyl)gramicidin (180 mg).

O-(N-(N-(N-(6-aminocaproyl)-6-aminocaproyl)-6-aminocaproyl)-6-aminocaproyl)gramicidin (11 mg), N-biotinyl-6-aminocaproic acid N-hydroxysuccinimide ester (2.1 mg) and triethylamine (0.71 µl) were dissolved in a mixture of DCM (0.5 ml) and methanol (0.5 ml) and the mixture was stirred for 2 h. The mixture was then evaporated to dryness. The residue was purified by preparative thin layer chromatography on silica (eluent=DCM/methanol/water/acetic acid 400:40:4:1) then chromatography on sephadex LH20 (eluent=methanol) to afford Ga5XSB (6 mg).

EXAMPLE 2

Figure 9:
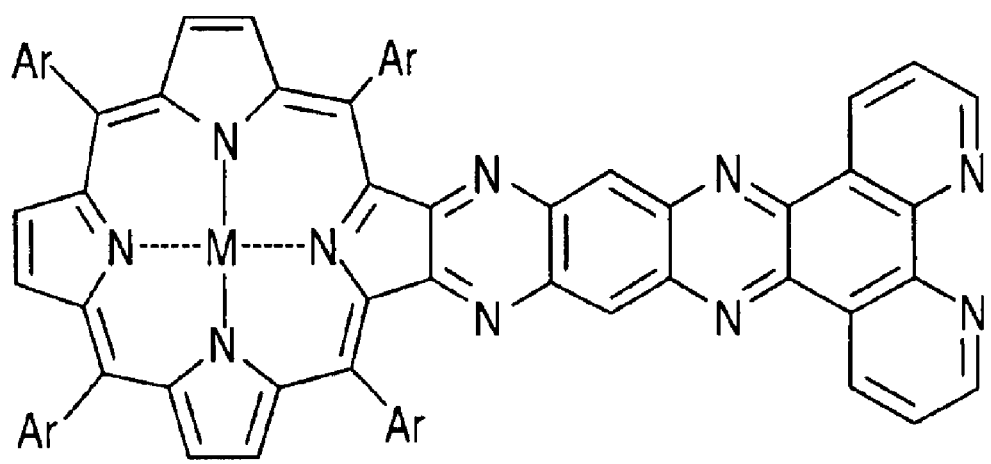
FIG. 9 shows the structure of the free base porphyrin-phenanthroline (M=2H; Ar=3,5-di butylphenyl) and the zinc chelated porphyrin-phenanthroline (M=Zn; Ar=3,5-di butylphenyl)

Gold layers deposited, if necessary using adhesion layers such as chromium, are deposited onto glass slides. The molecular wires shown in FIG. 9 (synthesised using the methodology of Crossley et al. J Chem Soc Chem Commun 1995 1921–1923) were dissolved in chloroform (approx 1 mg/mL), added into impedance wells and left at room temperature for one hour. The solution was removed and the wells thoroughly rinsed with chloroform (with the use of a nitrogen jet to remove the solvent rapidly). Top layers (TL) were then applied by injection (single cell aliquots were either 5 µL or 15 µL) according to the protocols listed in Table 1 below.

TABLE 1

| TL24 (with gramicidin) | TL110 (no gramicidin) | TL118 (Valinomycin) |
|---|---|---|
| 350 µL of 28 mM DPEPC | 150 µL of 28 mM GDPE | 500 µL ethanol |
| 14 µL of 10 µM Ga5XSB | 500 µL ethanol | 350 µL of 28 mM DPEPC |
| 150 µL of 28 mM GDPE | 500 µL ethanol | 350 µL of 28 mM DPEPC |
| 150 µL of 28 mM GDPE (ratio gramicidin:lipid 1:100,000) | | 40 µL of 10 mM valinomycin |

TABLE 1-continued

| TL24<br>(with gramicidin) | TL110<br>(no gramicidin) | TL118<br>(Valinomycin) |
|---|---|---|

Figure 10:
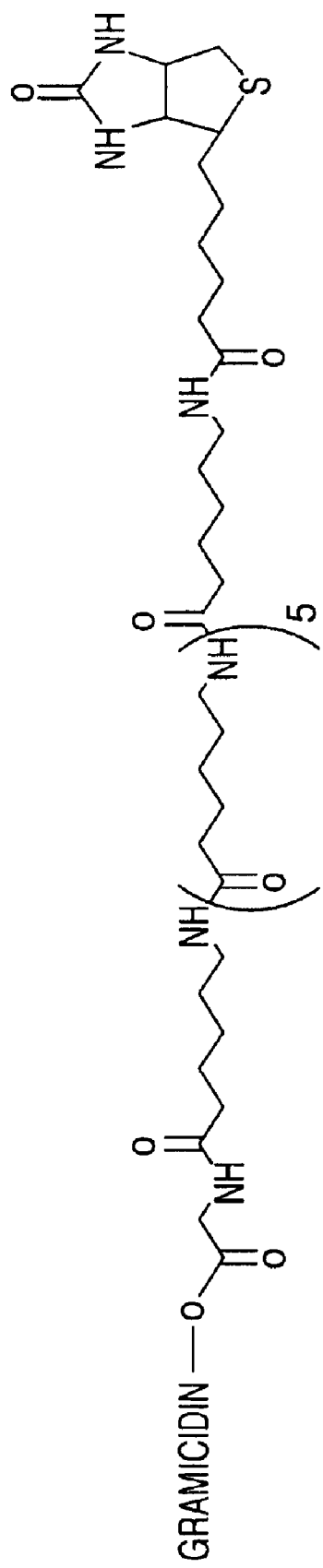
FIG. 10 shows the structure of Ga5XSB

DPEPC = diphytanylether phosphatidycholine
GDPE = glycerol diphytanylether
Ga5XSB = biotinylated gramicidin (FIG. 10)

When a molecular wire monolayer is formed, the cell impedance is generally observed to increase. This increase is significantly larger in the case of the zinc complexed compound and is referred to herein as the non-conducting molecular wire.

Application of a top layer also increases cell impedance regardless of the bottom layer used, including bare gold. The relative value of the impedance of the bilayer reflects the composition of its component monolayers. The impedance was determined as a function of frequency for conducting molecular wire (a), non-conducting Molecular wire (b), and bare gold (c) The impedance for the non-conducting wire was higher than that of a and c. Impedance spectra of samples with TL110 (no gramicidin) top layers assembled showed that an insulating layer was formed in each case with relative differences in the spectra largely reflecting the differences in the bottom layers.

The impedance spectra when a TL24 (with 1:100,000 gramicidin) top layer was assembled on conducting molecular wire (d), non-conducting molecular wire (e), and bare gold (f) was also determined. The inclusion of gramicidin into the lipid layer increases the conductance of the system. This demonstrates ion conduction through gramicidin monomers. It was observed that the magnitude of the impedance |Z| at 1 KHz was drastically increased due to the assembly of an additional layer, but |Z| at 1 Hz was only modestly increased.

The top layers may be single or multiple monolayers of lipid. The observed spectra were believed to be indicative of a single monolayer. The molecular wire SAM makes the surface hydrophobic which favours a single amphiphilic overlayer. The impedance at 1 KHz is approximately 1.2 K$\Omega$ for a top layer (with gramicidin) which is consistent with a bilayer system (bilayer here referring to a molecular wire monolayer plus a single lipid overlayer) and, thirdly, multiple, vigorous saline washes were administered; a process that would normally be expected to destroy a multiple monolayer system.

EXAMPLE 3

In a similar manner to the example of saline and gramicidin ion channels (Example 2) a valinomycin/potassium system was also constructed. Once again the impedance of the non-conducting molecular wire was found to be higher than that of the conducting wire or bare gold electrode. The addition of a top layer including valinomycin (TL118) resulted in a decrease in impedance in the presence of potassium.

These Examples demonstrate that a conducting layer of molecular wires can be formed and that this layer will function in combination with a lipid layer incorporating ionophores.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A biosensor comprising an electrode, a membrane and an intermediate region between at least portions of the membrane and the electrode; the biosensor comprising at least a first and a second zone, wherein each zone differs from each other zone in a property resulting from differences in the electrode, the intermediate region or combinations thereof within each zone; the membrane comprising a plurality of ionophores, at least a proportion of the ionophores being capable of lateral diffusion within the membrane; a plurality of first binding partner molecules attached to membrane elements positioned within the first zone such that the first binding partner molecules are prevented from diffusing laterally into the second zone, second binding partner molecules attached to the ionophores, the rate of lateral diffusion within the membrane of the first binding partner molecules and the second binding partner molecules being different.

2. A biosensor as claimed in claim 1, wherein the intermediate region functions as a reservoir or as a source or sink for ions.

3. A biosensor as claimed in claim 2 in which the intermediate region is an ionic reservoir.

4. A biosensor as claimed in claim 1 in which the property is selected from the group consisting of chemical, polarization, admittance, ionic reservoir capacity or redox potential.

5. A biosensor as claimed in claim 1 in which the electrode comprises a silicon silver composite or a silicon gold composite.

6. A biosensor as claimed in claim 1 in which the at least two zones of the biosensor comprise a pattern of islands.

7. A biosensor as claimed in claim 6 in which the islands are arranged to be insulated from each other so that they may be measured independently, or electrically interconnected for simultaneous measurement of all gating sites.

8. A biosensor as claimed in claim 6 in which the islands are provided on the electrode.

9. A biosensor as claimed in claim 1 in which the membrane elements are bolar lipids or membrane spanning proteins.

10. A biosensor as claimed in claim 1 in which the first and second binding pair molecules are antibodies or any active binding fragments of antibodies.

11. A biosensor as claimed in claim 1 in which the ionophore is gramicidin or analogues thereof or valinomycin.

12. A biosensor as claimed in claim 1 in which the membrane elements extend through the membrane.

13. A biosensor as claimed in claim 12 in which the membrane elements are attached to the electrode via attachment groups.

14. A method of assaying a sample for the presence of an analyte, the method comprising contacting a biosensor as claimed in claim 1 in which the first and second binding partner molecules bind to the analyte with the sample and measuring the conductivity of the membrane.

15. A biosensor comprising an electrode, a membrane and an intermediate region between at least portions of the membrane and the electrode; the biosensor comprising at least a first and a second zone, each zone being different from other zone in a property resulting from differences in the electrode, the intermediate region or combinations thereof within each zone; the membrane comprising a plurality of ionophores, at least a proportion of the ionophores being capable of lateral diffusion within the membrane; a plurality of first binding partner molecules attached to membrane elements positioned within the first zone such that the first binding partner molecules are prevented from diffusing laterally into the second zone, second binding partner molecules attached to the ionophores, the rate of lateral diffusion within the membrane of the first binding partner molecules and the second binding partner molecules being different, wherein the intermediate region functions as a reservoir or as a source or sink for ions and comprises molecular wires.

16. A biosensor as claimed in claim 15 in which the molecular wires have a porphyrinic or octathiophene based structure.

17. A biosensor as claimed in claim 16 in which the porphyrinic structure is comprised of a series of fused porphyrin rings with adjacent components of the wire fused through the [b] bond of the porphyrinic ring.

18. A biosensor as claimed in claim 17 in which the molecular wire includes bridging units between two adjacent porphyrin rings and between a porphyrin ring and end functional groups.

19. A biosensor as claimed in claim 18 in which the bridging units include an anthracene unit or tetraazaanthracene unit fused at the [b] and [e] bonds of the parent tetraazaanthracene system to the other components on the wire.

20. A biosensor as claimed in claim 15 in which the intermediate region comprising molecular wires (MW) are formed by self-assembly onto the electrode surface.

* * * * *